(12) United States Patent
Schadewaldt et al.

(10) Patent No.: US 11,684,801 B2
(45) Date of Patent: Jun. 27, 2023

(54) IMAGE-GUIDED RADIATION THERAPY

(71) Applicant: KONINKLIJKE PHILIPS N.V., Eindhoven (NL)

(72) Inventors: Nicole Schadewaldt, Hamburg (DE); Tim Nielsen, Hamburg (DE); Christian Buerger, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 236 days.

(21) Appl. No.: 16/492,186

(22) PCT Filed: Mar. 19, 2018

(86) PCT No.: PCT/EP2018/056816
§ 371 (c)(1),
(2) Date: Sep. 9, 2019

(87) PCT Pub. No.: WO2018/167324
PCT Pub. Date: Sep. 20, 2018

(65) Prior Publication Data
US 2020/0038683 A1    Feb. 6, 2020

(30) Foreign Application Priority Data
Mar. 17, 2017 (EP) .................................. 17161492

(51) Int. Cl.
*A61N 5/10* (2006.01)
(52) U.S. Cl.
CPC .......... *A61N 5/1037* (2013.01); *A61N 5/1038* (2013.01); *A61N 5/1049* (2013.01); *A61N 2005/1055* (2013.01)

(58) Field of Classification Search
CPC ........ A61N 5/103–1038; A61N 5/1039; A61N 2005/1041; A61N 2005/1055
See application file for complete search history.

(56) References Cited

U.S. PATENT DOCUMENTS

| | | |
|---|---|---|
| 6,473,634 B1 | 10/2002 | Barni |
| 8,306,185 B2 | 11/2012 | Bal et al. |
| 8,306,297 B2 | 11/2012 | Fu |
| 10,806,947 B2 | 10/2020 | Foo |

(Continued)

FOREIGN PATENT DOCUMENTS

| | | |
|---|---|---|
| JP | 2017035343 A | 2/2017 |
| WO | WO0120552 A1 | 3/2001 |
| WO | WO2016094284 A1 | 6/2016 |

*Primary Examiner* — Thaddeus B Cox

(57) ABSTRACT

For delivering an image-guided radiation therapy treatment to a moving structure included in a region of a patient body a series of first images of the region of the patient body in different phases of a motion of the structure is acquired in accordance with a first imaging mode. The series of first images is associated with a series of second images of the patient body in essentially the same phases of the motion of the target structure, the second images being acquired in a second imaging mode. During the treatment, a third image is acquired using the second imaging mode during the radiation therapy treatment and a continuation of the radiation therapy treatment is planned on the basis of data relating to one of the first images selected on the basis of a comparison between the third image and the second images associated with the first images.

20 Claims, 1 Drawing Sheet

(56) References Cited

U.S. PATENT DOCUMENTS

| | | |
|---|---|---|
| 10,946,214 B2 | 3/2021 | Pekar |
| 2006/0074292 A1 | 4/2006 | Thomson |
| 2015/0139503 A1 | 5/2015 | Kabus |
| 2016/0082288 A1 | 3/2016 | Vahala |
| 2016/0310761 A1 | 10/2016 | Li |
| 2017/0014645 A1* | 1/2017 | Foo ................. A61B 5/0035 |
| 2017/0043184 A1* | 2/2017 | Mori ................. A61N 5/1077 |
| 2017/0095197 A1* | 4/2017 | Kleiner ............. A61B 6/486 |
| 2017/0106208 A1* | 4/2017 | Gauthier ........... A61N 5/1037 |
| 2017/0216627 A1* | 8/2017 | Brooks ............. A61N 5/1048 |
| 2019/0038919 A1* | 2/2019 | Lachaine .......... A61N 5/1077 |
| 2019/0080459 A1* | 3/2019 | Lachaine .......... A61N 5/1045 |

* cited by examiner

IMAGE-GUIDED RADIATION THERAPY

FIELD OF THE INVENTION

The invention generally relates to image-guided radiation therapy. More specifically, the invention relates to a treatment system for delivering an image-guided radiation therapy treatment and a method for operating the system. Further, the invention relates to a system and method for preparing an image-guided radiation therapy treatment. Moreover, the invention is related to a computer program for carrying out the methods.

BACKGROUND OF THE INVENTION

In external beam radiation therapy, ionizing radiation is applied to target structures, such as tumors, within patients' bodies in order to control growth of or kill cancer cells. In more advanced types of radiation therapy, precise doses of radiation are applied to regions of the patient's body. In this respect, it is typically the goal to deliver a sufficiently high radiation dose to the target structure and to spare sensitive structures, which are usually also referred to as organs at risk (OAR), in the vicinity of the target structure as far as possible.

The treatment parameters for controlling the irradiation of the patient are defined in a treatment plan, which particularly specifies the direction and shape of the radiation beam for irradiating the patient as a function of the time during the treatment. The treatment plan may be determined in an inverse planning procedure. In this procedure, treatment goals may be specified which comprise requirements for the radiation dose delivered to the target structure and the OARs during the treatment. Then, an optimization process is carried out to find a treatment plan which results in a distribution of the accumulated dose delivered to the patient, which fulfills the treatment goals. In the planning procedure, one or more three-dimensional planning image(s) of the body region of interest are used which represent the anatomical configuration of the targets structure and the OARs. The image(s) may be acquired using x-ray tomography or magnetic resonance (MR) imaging or another suitable imaging modality.

Conventionally, the planning procedure is carried out on the basis of a stationary shape and position of the target structure and the OARs as shown in the planning image(s). However, the shape and/or position of the target structure and the OARs usually change during the radiation treatment. So the target structure and the OARs may move during the treatment, e.g. due to respiration of the patient. Because of such variations in the shape and/or position of the target structure and the OARs, safety margins are usually added to the target structure when generating the treatment plan. However, despite these safety margins the original treatment plan may not be accurate throughout the complete treatment so that the treatment goals may not be met on the basis of this treatment plan.

In order to avoid this drawback of conventional radiation therapy treatment, image-guided radiation therapy has been suggested. In accordance with this approach, images of the target structure are captured during the course of the radiation therapy in order to determine the changed shape and/or position of the target structure and of the structure at risk. Using these images, the continuation of the treatment is planned in intervals during the treatment. In particular, it is determined whether the treatment goals can be fulfilled on the basis of the active treatment plan, and a re-planning procedure may be carried out to adapt the treatment plan if the treatment goals cannot be fulfilled on the basis of the active treatment plan due to the changed shape and/or position of the target structure.

In order to determine whether the treatment goals can be fulfilled, the accumulated radiation dose previously delivered to the target structure should be determined on a voxel-by-voxel basis, where a voxel corresponds to the volume element of the images of the region of interest. Based on these accumulated dose values and the doses to be deposited in each voxel during the remainder of the treatment in accordance with the active treatment plan, it can be determined whether the treatment goals can be fulfilled on the basis of the active treatment plan. Moreover, if the treatment plan is adapted, the accumulated radiation dose previously delivered to the target structure and the OARs in accordance with the previous treatment plan(s) has to be taken into consideration in the determination of the modified treatment plan.

In order to accurately perform the dose accumulation, each voxel representing a certain portion of the target structure or an OAR in the current image used for determining the modified treatment plan should be mapped to the image(s) underlying the previous treatment plan(s). This means that for each relevant voxel of the current image, the volume in the planning image(s) underlying the previous treatment plan(s) is determined, which corresponds to the same portion of the target structure or an OAR. On the basis of this mapping, it is possible to determine the accumulated radiation dose already delivered to the voxel in accordance with the previous treatment plan.

In order to carry out dose accumulation in such a way, deformable image registration (DIR) may be applied. In DIR, voxels of two images are transformed into the same coordinate space, which may particularly be the coordinate space of one of the images, and the transformation can involve translations and rotations of voxels as well as deformations of voxels' shapes. Therefore, DIR allows for determining so-called deformation vector fields which correspond to the aforementioned mapping of the voxels of the current image to the image(s) underlying the treatment plan.

However, an accurate DIR can usually only be determined for images having identical or at least very similar characteristics such as resolution and contrast. However, the planning images acquired prior to the delivery of the treatment and the images acquired during the treatment are often quite different in this respect and the images acquired during the treatment have poorer quality. This is particularly true for MR images. In order to acquire such images sufficiently fast during the treatment, special acquisition sequences may be applied which yield MR images having a lower resolution and lower contrast than the MR planning images used for the initial planning prior to the delivery of the treatment. These images are acquired on the basis of slower acquisition sequences yielding MR images with high resolution and contrast ensuring an accurate treatment planning.

If the DIR is carried out on the basis of images differing in their characteristics, the resulting deformation vector field usually has a non-negligible error. As a consequence, the planning of the continuation of the treatment on the basis of the deformation vector field has inaccuracies resulting in an inadequate dose distribution delivered to the target structure and/or the OARs.

US 2006/0074292 A1 describes dynamic tracking of moving targets. Treatment targets such as tumors or lesions, located within an anatomical region that undergoes motion (which may be periodic with cycle P), are dynamically tracked. A 4D mathematical model is established for the non-rigid motion and deformation of the anatomical region, from a set of CT or other 3D images. The 4D mathematical model relates the 3D locations of part(s) of the anatomical region with the targets being tracked, as a function of the position in time within P. Using fiducial-less non-rigid image registration between pre-operative DRRs and intra-operative x-ray images, the absolute position of the target and/or other part(s) of the anatomical region is determined. The cycle P is determined using motion sensors such as surface markers. The radiation beams are delivered using: 1) the results of non-rigid image registration; 2) the 4D model; and 3) the position in time within P.

SUMMARY OF THE INVENTION

It is an object of the invention to improve the planning of the continuation of the treatment during the delivery of a radiation therapy treatment on the basis of real-time images acquired during the delivery of the treatment.

In one aspect, the invention suggests a treatment system for delivering an image-guided radiation therapy treatment to a moving structure included in a region of a patient body on the basis of a treatment plan. The treatment system comprises a receiving unit for receiving a series of first images of the region of the patient body in different phases of a motion of the structure, the series of first images being associated with a series of second images of the patient body in essentially the same phases of the motion of the target structure, the first images being acquired in accordance with a first imaging mode and the second images being acquired in a second imaging mode differing from the first imaging mode and each second image being associated with a first image pertaining to the same phase of the motion of the target structure. The treatment system further comprises an imaging unit controllable to acquire a third image of the patient using the second imaging mode during the radiation therapy treatment and an evaluation unit configured to plan a continuation of the radiation therapy treatment upon the acquisition of the third image. The evaluation unit is configured to plan a continuation of the treatment on the basis of data relating to one of the first images and to select said first image on the basis of a comparison between the third image and the second images associated with the first images.

The data related to the first image may comprise the first image and/or a deformation vector field for carrying out DIR between the first image and a reference image, particularly as will be described herein below.

Since the continuation of the treatment is not directly planned on the basis of a third image acquired in accordance with the second imaging mode during the radiation therapy treatment but on the basis of a first image acquired in accordance with the first imaging mode, it is possible to use an image for the planning of the continuation of the treatment, which has a better quality than the images acquired during the treatment. Moreover, since the first image is identified on the basis of a comparison between the second images associated with the first images and the third image acquired during the treatment, it is possible to select the first image in accordance with the actual anatomical configuration of the body region including the structure as shown in the third image. Further, since the second images and the third image are acquired in accordance the second image mode, they have similar characteristics so that the comparison of these images is simplified.

In one embodiment, the second imaging mode is selected such that it allows for a faster image acquisition compared with the first imaging mode. This allows for a fast acquisition of the third images during the radiation therapy treatment.

In a further embodiment, the first images are three-dimensional images and the second and third images are three-dimensional, two-dimensional or one-dimensional images. Three-dimensional second images allow for capturing complex three-dimensional transformations of the structure to be treated. Two-dimensional and one-dimensional images have the advantage that they can be acquired faster, particularly during the radiation delivery treatment.

In case the second images are two-dimensional or one-dimensional images, image characteristics of the third images, such as the angle of view and/or the field of view, may differ from the corresponding characteristics of the second images. Therefore, the series of second images may optionally comprise plural second images for one or more of the motion phases. For each of these motion phases, the plural second images may be acquired for different angles of view and/or different fields of view. Hereby, a more robust selection of the associated first images can be achieved on the basis of a third image.

In one embodiment, the evaluation unit is configured to identify a motion phase associated with at least one second image that best matches the third image in accordance with a predefined criterion and to identify the first image associated to the identified motion phase as the first image on the basis of which the continuation of the radiation therapy treatment is planned.

In a further embodiment, the evaluation unit is configured to plan the continuation of the treatment on the basis of an estimated accumulated radiation dose delivered to the structure in the radiation therapy treatment, the accumulated dose being determined based on a deformation vector field for performing deformable image registration between the identified first image and a reference image acquired in accordance with the first imaging mode.

In a related embodiment, the accumulated dose is further determined on the basis of a further deformation vector field for performing deformable image registration between the third image and the at least one second image associated with the identified motion phase. The further deformation vector field quantifies the differences between the current location and contour of the structure as shown in the third image and the locations and contours shown in the selected second image and the associated first image. This corresponds to an error of the deformation vector field for performing deformable image registration between the identified first image and the reference image, which is corrected by means of the second deformation vector field in this embodiment.

In a further related embodiment, the treatment plan is generated on the basis of a planning image of the region of the patient body in one phase of the motion of the structure, the planning image corresponding to the reference image. Moreover, the planning image may correspond to one of the first images. This means that the treatment plan is generated on the basis of one of the first images. However, this does not necessarily have to be the case and the planning image used for generating the treatment plan may likewise be acquired independently of the first images.

Based on the estimated accumulated radiation dose delivered to the structure, the evaluation unit may particularly determine whether the treatment goals for the radiation therapy treatment can be fulfilled by continuing the treatment using the treatment plan. This determination is comprised in the planning of the continuation of the treatment.

In case the evaluation determines that the treatment goals can not be fulfilled by continuing the treatment using the treatment plan, the evaluation unit may determine an adapted treatment plan. The adapted treatment plan may be determined on the basis of the identified first image and/or on the basis of the estimated accumulated radiation dose. Thereupon, the adapted treatment plan may be provided for continuing the treatment.

Further, the imaging unit may comprise an MR imaging device and the first and second imaging modes include an image acquisition using the MR imaging device.

In a further aspect, the invention suggests a treatment preparation system for preparing an image-guided radiation therapy treatment of a moving structure included in a region of a patient body. The treatment preparation system comprises an imaging unit controllable to acquire a series of first images of the region of the patient body in different phases of a motion of the target structure, the first image being acquired in accordance with a first imaging mode. The imaging unit is further controllable to acquire a series of second images of the region of the patient body in essentially the same phases of the motion of the target structure, the second images being acquired in accordance with second imaging mode. Further, the treatment preparation system is configured to associate each second image to a first image pertaining to the same phase of the motion of the structure as the second image and to provide the second images and data related to the associated first images for use in planning a continuation of the radiation therapy treatment during the treatment. The data related to the first image may comprise the first image itself and/or a deformation vector field for carrying out DIR between the first image and the reference image.

In one embodiment of the treatment preparation system, the imaging unit is controllable to alternately acquire the first and second images.

Moreover, one embodiment includes that the treatment preparation system further comprises a planning unit configured to generate a treatment plan for the radiation therapy treatment on the basis of one of the first images and to provide the treatment plan for use in controlling a delivery of the radiation therapy treatment.

In a further aspect, the invention proposes a method for operating a treatment system for delivering an image-guided radiation therapy treatment to a moving structure included in a region of a patient body on the basis of a treatment plan. The method comprises:

receiving a series of first images of the region of the patient body in different phases of a motion of the structure, the series of first images being associated with a series of second images of the patient body in essentially the same phases of the motion of the target structure, the first images being acquired in accordance with a first imaging mode and the second images being acquired in accordance with a second imaging mode differing from the first imaging mode, each second image being associated with a first image pertaining to the same phase of the motion of the target structure, acquiring a third image of the patient using the second imaging mode during the delivery of the radiation therapy treatment, and planning a continuation of the radiation therapy treatment upon the acquisition of the third image on the basis of data relating to one of the first images, said first image being selected on the basis of a comparison between the third image and the second images associated with the first images.

In a further aspect, the invention suggests a method for preparing an image-guided radiation therapy treatment of a moving structure included in a region of a patient body. The method comprises:

controlling an imaging unit to acquire a series of first images of the region of the patient body in different phases of a motion of the target structure, the first image being acquired in accordance with a first imaging mode, controlling the imaging unit to acquire a series of second images of the region of the patient body in essentially the same phases of the motion of the target structure, the second images being acquired in accordance with a second imaging mode, associating each second image to a first image pertaining the same phase of the motion of the structure as the second image, and providing the second images and data related to the associated first images for use in planning a continuation of the radiation therapy treatment during the treatment. In addition to the method for operating the treatment system and the method for preparing the treatment, the invention suggests a further method comprising the steps of the method for operating the treatment system and the method for preparing the treatment.

In a further aspect, the invention suggests a computer program comprising program code means for causing a computer device to carry out a method as defined in the claims when the computer program is executed on the computer device.

It shall be understood that the claimed treatment system, the claimed treatment preparation system, the claimed method for operating a treatment system, the claimed method for preparing an image-guided radiation therapy treatment, and the claimed computer program have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
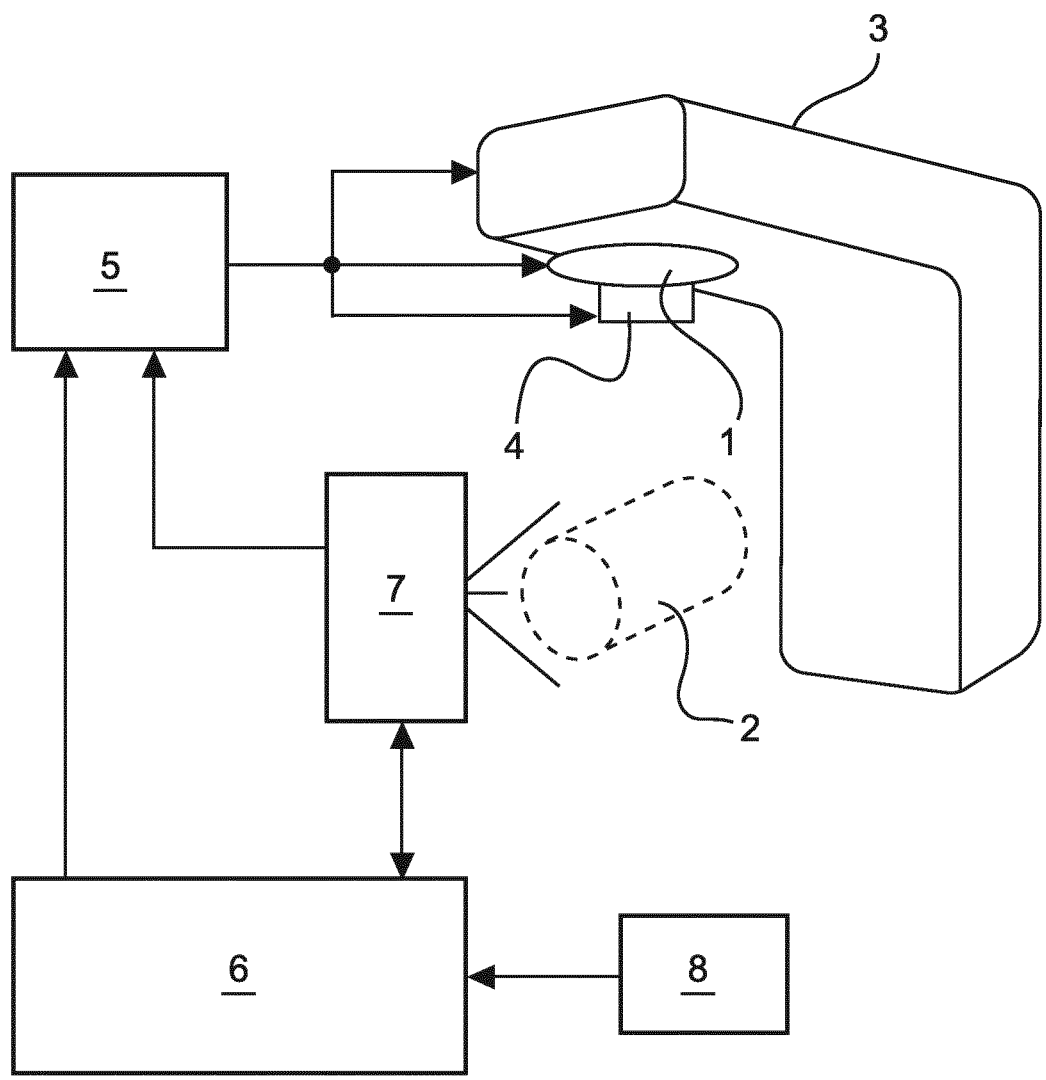
FIG. 1 schematically and exemplarily shows components of a treatment system for delivering an image-guided radiation therapy, and FIG. 2 schematically and exemplarily shows components of a planning system for planning the radiation therapy treatment.

FIG. 1 schematically and exemplarily illustrates an embodiment of a treatment system for delivering image-guided radiation therapy treatments of a target structure of a patient body. The target structure may particularly be a tumor. The treatment is carried out on the basis of an initial treatment plan which is generated prior to the treatment in a planning system which is schematically and exemplarily shown in FIG. 2 in one embodiment. During the delivery of the radiation therapy treatment, the treatment system may determine modified treatment plans in order to adapt the initial treatment plan to anatomical changes of the region of the patient body including the target structure to be treated, if necessary.

The radiation treatment may be delivered in a plurality of fractions, where the fractions may be delivered to the structure on consecutive days or in another cycle. Changes of the anatomical configuration of the relevant region of the patient body can occur in between the treatment fractions (so-called inter-fractional changes) and during the treatment fractions (so-called intra-fractional changes). In the treatment system shown in FIG. 1, it is evaluated during the treatment whether particularly intra-fractional changes require a re-planning of the treatment or whether the treatment goals can be fulfilled on the basis of the initial treatment plan despite such changes. Such changes can particularly be due to motion of the target structure and/or surrounding OARs during the delivery of the treatment, which may be caused by respiratory movement of the patient body, for example. In case such intra-fractional changes require a re-planning of the treatment, the system may further be enabled to adapt the treatment plan to the changes. In addition, the treatment plan may be adapted to inter-fractional changes of the anatomy of the relevant region of the patient body.

In the embodiment illustrated in FIG. 1, the radiation therapy system comprises a radiation source 1, which can be operated to emit ionizing radiation to be delivered to the target structure within the patient body positioned in a treatment zone 2. In the treatment zone 2, the patient may be positioned on a suitable support, such as a patient table, which is not shown in the figures. The relative position and orientation of the radiation source 1 with respect to the body or target structure can be varied over a certain range of positions and orientations. For this purpose, the radiation source 1 may be mounted on rotatable gantry 3 so that the radiation source 1 can be rotated around the treatment zone 2 within a certain angular range, which may be 360° or less. In addition, the gantry 3 and/or the patient support may be movable back and forth in a direction parallel to the rotation axis of the gantry 3 and, it may further be possible to rotate the support around an axis perpendicular to the rotation axis of the gantry 3.

The radiation source 1 may include a linear particle accelerator or another radiation source for producing an ionizing radiation beam. One example of another radiation source is a radioactive source, such as a cobalt source. The radiation source 1 may be provided with a collimator 4 for shaping the radiation beam. The collimator 4 may particularly allow for varying the radiation intensity across the radiation beam in a defined way. For this purpose, the collimator 4 may be configured as a multi-leaf collimator.

During delivery of the radiation treatment, the configuration of the collimator 4 is usually changed based on the treatment plan so that the radiation beam is delivered with a time-varying shape. In one implementation, the radiation treatment is delivered in accordance with successive so-called segments, where each segment corresponds to a certain collimator configuration or beam shape. In between two segments, the collimator configuration is changed from the configuration of the first of the segments to the configuration of the second of the segments. During this period, the radiation beam may be turned off (this is usually also referred to as step-and-shoot approach). Likewise, it is possible to continuously change the collimator configuration in accordance with the segments without interrupting the radiation beam. This approach is applied in so-called volume modulated arc therapy (VMAT), for example.

For controlling the radiation source 1, the collimator 4 and the patient support during the treatment, the treatment system includes a control unit 5. Preferably, the control unit 5 is implemented in a computer device including a microprocessor for executing a control program comprising the control routines carried out by the control unit 5.

During the radiation therapy treatment, the control unit 5 particularly controls the gantry 3, the patient support and the operation of the radiation source 1 and the collimator 4 on the basis of a treatment plan which specifies the relevant irradiation parameters including the collimator configuration and the energy and/or intensity of the radiation beam emitted by the radiation source 1. In this respect, an initial treatment plan may be provided to the treatment system by a planning system that will be described in more detail herein below. The treatment system is further configured to assess during the treatment whether the treatment goals can be fulfilled on the basis of the initial treatment plan despite of changes of the anatomical configuration of the region of the patient body comprising the target structure and to adapt the initial treatment plan to such changes of the anatomical configuration in case the treatment goals cannot be fulfilled on the basis of the initial treatment plan.

For carrying out this assessment and for adapting the treatment plan, the treatment system comprises an evaluation unit 6. The evaluation unit 6 carries out the assessment of whether the treatment plan allows for fulfilling the treatment goals and a possible re-planning of the treatment on the basis of images acquired using an imaging unit 7 integrated into the treatment system, which may particularly be configured as an MR imaging unit. Further, the assessment of whether the treatment plan allows for fulfilling the treatment goals and the possible re-planning of the treatment are made on the basis of image data and on the basis of further information provided to the evaluation unit 6 via a receiving unit 8 associated with the evaluation unit 6. Preferably, the evaluation unit 6 is implemented as a software program comprising routines for assessing whether the treatment goals can be fulfilled and for performing the adaptation of the treatment plan and being executed on a computer device included in the treatment system. In this respect, the same computer device may also implement the control unit 5 as explained above. However, the evaluation unit 6 and the control unit 5 may likewise be implemented in different computer devices.

The imaging unit 7 is arranged and configured to acquire images of the relevant region of the patient body while the patient is positioned in the treatment zone in the predefined position for the treatment. In order to assess whether the treatment goals can be fulfilled on the basis of the treatment plan and to adapt the treatment plan to changes of the anatomical configuration of the relevant region of the patient body, the imaging unit 7 is configured to acquire images during the delivery of the radiation therapy treatment in accordance with a special imaging mode which allows for a sufficient fast acquisition of images. This imaging mode is also referred to as fast imaging mode herein below.

The fast imaging mode particularly differs from the imaging mode used for acquiring the planning image in the planning system described below. This imaging mode is also referred to as high-quality imaging mode and images acquired using this imaging mode are also referred to as high-quality images herein. In order to increase the acquisition speed, the fast imaging mode may particularly yield images having a lower resolution and/or contrast compared with the high-quality images. Moreover, the high-quality images are preferably three-dimensional. In contrast, the navigation images may likewise be two-dimensional or one-dimensional images in implementations of the treatment system.

In case the imaging unit 7 is configured as an MR imaging unit, the fast imaging mode may particularly comprise the use of T1-weighted or proton density (PD)-weighted pulse sequences. Such pulse sequences allow for faster acquisition times. However, they yield images having relatively low contrast. The high-quality imaging mode for an MR imaging mode may also comprise the use of T2-weighted pulse sequences and/or Fluid Attenuated Inversion Recovery (FLAIR) pulse sequences, for example.

In addition to the fast imaging mode, the imaging unit 7 of the treatment system may also support the high-quality imaging mode. This imaging mode may be applied in case the treatment system is operated as a planning system as will be explained herein below. In this case, the high-quality imaging mode is employed in order to acquire the planning image used for generating the initial treatment plan. Moreover, the high-quality imaging mode may be applied to acquire images used for adapting the treatment plan to inter-fractional changes of the anatomical configuration of the relevant body region of the patient. Such images may be acquired prior to the delivery of a treatment fraction and on the basis of such images the evaluation unit 6 may perform a re-planning procedure in order to generate a modified treatment plan on the basis of the initial treatment plan, which modified treatment plan is adapted to the changes of the anatomical configuration of the target structure and/or the OARs shown in the initial planning image and in the current real-time image.

Figure 2:
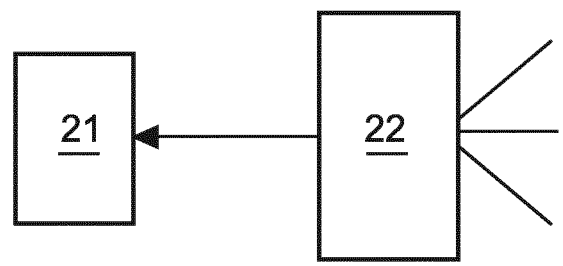

The planning system schematically and exemplarily shown in FIG. 2 is configured to generate an initial treatment plan prior to the delivery of the radiation therapy treatment. The planning system comprises a planning unit 21 which provides routines for generating a treatment plan. It may be implemented as a software program executed on a computer device of the planning system. Further, the planning system comprises an imaging unit 22 for acquiring images of the region of a patient body including the target structure to be treated and surrounding OARs. The imaging unit 22 is preferably configured in accordance with the same imaging modality as the imaging unit 7 of the treatment system. Moreover, the imaging unit 22 supports a high-quality imaging mode. This imaging mode is particularly used in order to acquire a planning image on the basis of which the initial treatment plan is generated. In addition, the imaging unit 22 may support the fast imaging mode and this imaging mode may be used in order to acquire navigation images already in the planning phase as will be explained herein below.

In one embodiment, the planning system is spatially separated from the treatment system. However, in a further embodiment the planning system is integrated into the treatment system. In this case, the imaging unit 7 of the treatment system is also used in order to acquire the planning image. Moreover, the planning unit 21 may be implanted in a computer device of the treatment system, which may be a computer device including the control unit 5 and/or the evaluation unit 6, or a separate computer device.

In the planning unit 21, the initial treatment plan is generated using a three-dimensional planning image of the relevant planning volume within the patient body including the target structure and OARs surrounding the target structure. The planning image shows one anatomical configuration of the changing anatomical structure of the planning volume. In the planning image, the target structure and the OARs are delineated. The delineation may be carried out using any suitable procedure known to the person skilled in the art and may be configured as a manual, semi-automatic or automatic delineation procedure. Moreover, safety margins are usually added to the delineations in order to generate effective positions and shapes of the target structure and the OARs on the basis of which the treatment plan is calculated. These safety margins account for changes of the position and/or shape of the target structure and/or the OARs during the treatment.

On the basis of the planning image, the initial treatment plan may be generated in accordance with an inverse planning procedure. Such a procedure is carried out on the basis of treatment goals. The treatment goals particularly specify a radiation dose to be delivered to the target structure. With respect to the target structure, there may be specified a uniform dose to be delivered to the target structure or there may be specified varying dose goals for different regions of the target structure. Corresponding treatment goals may be specified in a clinical prescription for the patient, which is prepared on the basis of a clinical diagnosis preceding the radiation therapy treatment. In addition, the treatment goals specify requirements for the radiation dose delivered to OARs. These treatment goals may likewise be included in the prescription for the patient, or they may be specified in general rules relating to the radiation treatment. The treatment goals relating to the target structure may particularly specify minimum radiation doses to be delivered to portions of the target structure. The treatment goals relating to the OARs may specify maximum radiation doses to be delivered to the OARs.

The treatment goals are to be fulfilled during the radiation therapy treatment within predefined boundaries. This means that deviations from the treatment goals are generally acceptable, if they do not exceed predefined thresholds. In order to determine a treatment plan such that the treatment goals are fulfilled within the predefined boundaries, an optimization problem is formulated and the planning unit 21 at least approximately solves this optimization problem. In so doing, the planning unit 21 determines a treatment plan which corresponds to a dose distribution in the planning volume, which fulfills requirements set out in the treatment goals within the boundaries. The dose distribution specifies the spatial distribution of the radiation dose values in the planning volume, i.e. it assigns to each voxel of the planning volume the radiation dose delivered to this voxel, where a voxel corresponding to a volume element of the planning image.

In order to find such a treatment plan, an operator-guided iterative optimization procedure may be applied in which the planner may modify the treatment goals and/or other parameter of the calculation in order to arrive at the optimum treatment plan. In each step of this procedure, the planning unit 21 automatically calculates a preliminary treatment plan by approximating a solution of the optimization problem. Then, the planning unit 21 determines the dose distribution corresponding to this treatment plan and visualizes the dose distribution to the treatment planner operating the planning unit 21. The planner reviews the dose distribution to decide whether he/she is satisfied with the dose distribution or not. If the planner is satisfied in one step, the treatment plan calculated in this step is used as the final treatment plan. If the user is not satisfied, the optimization problem is modified in accordance with changes specified by the user as a result of his/her review. Then, the planning unit 21 calculates a new preliminary treatment plan in the next iteration step.

The initial treatment plan may be used for controlling the treatment system during the delivery of the radiation treatment. However, the initial treatment plan is generated for a certain anatomical configuration of the region of the patient body including the target structure and the surround OARs. This anatomical configuration may change during the treatment, particularly due to motion of the target structure and/or the OARs. Due to the aforementioned safety margins and allowed deviations from the prescribed dose goals, changes of the anatomical configuration of the relevant body region do not necessarily have the consequence that the treatment goals can no longer be fulfilled. However, this may be the case if larger changes occur. Therefore, it is assessed during the treatment whether the treatment goals can be fulfilled on the basis of the initial treatment plan despite anatomical changes of the region including the target structure. If this is not the case, adaptations may be made to the initial treatment plan in the evaluation unit 6 of the treatment system. Moreover, the adapted plan may be further modified in response to anatomical changes during the treatment.

The assessment of whether the treatment goals can be fulfilled on the basis of an active treatment plan (which may be the initial treatment plan or an already adapted treatment plan) particularly involves an estimation of the accumulated radiation dose already delivered to each voxel of the planning volume during the treatment in accordance with the actual anatomical configuration of the region including the target structure. Based on these accumulated dose values and the doses to be deposited in each voxel during the remainder of the treatment in accordance with the active treatment plan it can be determined whether the treatment goals can be fulfilled within the predefined boundaries on the basis of the active treatment plan.

In order to carry out dose accumulation, the dose delivered to the voxels of the target structure and the OARs is computed for temporal segments of the treatment and each voxel of the target structure and the OARs is preferably tracked over the course of the treatment, i.e. in the initial planning image and on the basis of images acquired during the treatment. On the basis of this information, the accumulated dose may be determined for each relevant voxel.

For calculating the radiation dose delivered to the target structure and the OARs several procedures are known the person skilled in the art. In general, this dose is calculated on the basis of the active treatment plan in each relevant temporal segment and on the basis of an image acquired during the treatment which represents the positions and shapes of the target structure during each relevant temporal segment. In accordance with one exemplary procedure, the delivered dose for a segment may be calculated by mapping the dose distribution for the segment resulting from the treatment plan in accordance with the anatomical configuration at the time of the generation of the treatment plan to the image acquired during the treatment. In a further exemplary procedure, the dose delivered during each relevant temporal segment is calculated on the basis of the fluence map corresponding to the active treatment plan, which quantifies the intensity of the radiation emitted by the radiation source 1, and on the basis of the image acquired during the treatment.

For tracking the relevant voxels, DIR may be carried out between a reference image and images showing the anatomical configuration of the region including the target structure and the OARs during the treatment, where the reference image may correspond to the image on the basis of which the initial treatment plan is determined. The DIR may be carried out using any suitable DIR algorithm known to the person skilled in the art. For instance, suitable DIR algorithms for a region including the lung of patient are described in the publication N. Samavati et al., "Effect of deformable image registration uncertainty on lung SBRT dose accumulation", Med. Phys. 43, 233 (2016) and the references cited therein. The output of the DIR is a deformation vector field which transforms an image showing the anatomical configuration of the region including the target structure and the OARs to the reference image. Using this deformation vector field, the dose delivered to each relevant voxel in accordance with the adapted treatment plan can be mapped to the corresponding voxel of the reference image in order to carry out dose accumulation.

In order to accurately perform the dose accumulation, the DIR is preferably carried out using high-quality images allowing to accurately identify the position and shape of the target structure and/or the OARs. Moreover, the images preferably have essentially the same characteristics with respect to contrast and resolution. This means that the DIR is preferably carried out based on images acquired using the high-quality imaging mode in order to guarantee an accurate dose accumulation. However, it is not possible to acquire real-time images using the high-quality imaging mode during the treatment, since there is not sufficient time to acquire images using this mode. Therefore, the dose accumulation is carried out in response to images acquired using the fast imaging mode.

However, the dose accumulation is not directly carried out on the basis of these images. Rather, each of the images acquired during the treatment is used in order to identify one of a plurality of high-quality images acquired in advance using the high-quality imaging mode such that the identified image at least approximately shows the target structure and/or the OARs in the same phase of its motion as the acquired real-time image. DIR is performed between the identified high-quality image and the relevant reference image to determine a deformation vector field for transforming the identified high-quality image to the reference image. The dose accumulation is then carried out on the basis of this deformation field.

In order to prepare such a dose accumulation procedure, a series of high-quality images is acquired prior to the relevant treatment fraction. The high-quality images of this series preferably shows the region of the patient body including the target structure and the surround OARs in different phases of their motion. Preferably, the motion occurring in the course of the acquisition of the high-quality images repeats itself during the delivery of the treatment. Therefore, the suggested procedure is especially suitable for dose accumulation in case of periodic motions of the target structure and the OARs occurring during the treatment and at the time of the acquisition of the series of high-quality images. One example of such a periodic motion is motion induced by the breathing of the patient. Such motion particularly occurs when the target structure is located in the thorax as it is the case for a lung cancer, for example.

In addition to the series of high-quality images, a further series of images is acquired using the low-quality imaging mode. These images are also referred to as navigation images herein. The navigation images are preferably acquired essentially for the same phases of the motion of the target structure and the OARs as the high-quality images. Thus, series of high-quality images and navigation images are acquired which include a high-quality image and a navigation image for each of a number of different phases of the motion. In order to acquire the series of high-quality and navigation images in such a way, the high-quality-images and the navigation images may be acquired alternately. For this purpose, the imaging unit used for acquiring the images may be controlled to alternately acquire images in accordance with the high-quality imaging mode and the fast imaging mode.

As said above, the high-quality images are three-dimensional images having a high contrast and resolution. The navigation images have a lower contrast and/or resolution. Moreover, the navigation images may also be three-dimensional images. However, it is likewise possible that the navigation images are one-dimensional or two-dimensional images. Three-dimensional navigation images particularly allow for capturing complex deformations of the target structure and/or of OARs. This is particularly advantageous in view of structures undergoing such deformations such as, for example, the liver or the pancreas. Two-dimensional navigation images usually still have a relatively high spatial resolution so that such images still allow for localizing small structures with a relatively high accuracy. One-dimensional navigation images have the advantage that they can be very quickly acquiring during the delivery of the treatment.

Taking these characteristics of the dimensionalities of the navigation into consideration, the dimensionality to be used is selected in accordance with the particularly clinical application. In particular, the dimensionality may be selected in accordance with the type of the target structure to be treated and the OARs. The selection may be made in such a way that navigation images having a lower dimensionality are generally preferred in order to ensure a high acquisition speed and that a higher dimensionality is only selected in case navigation images having a lower dimensionality do not allow for sufficiently localizing the target structure and/or the OARs.

In case the navigation images are two-dimensional or one-dimensional images, these images are acquired in such a way that they show a section of the region including the target structure and the OARs which comprise sufficiently strong contrasts for determining the position and/or shape of the target structure and OARs. This ensures a robust and fast selection of a navigator image on the basis of a real-time image acquired during the treatment as will be explained herein below. In order to choose an appropriate section of the relevant region of the patient body and set the field-of-view of acquiring the navigation images accordingly, a three-dimensional scout scan may be performed prior to the acquisition of the series of high-quality images and navigation images.

Moreover, in case two-dimensional or one-dimensional navigation images are used, the series of navigation images may comprise plural images for some or each of the motion phases. For each of these motion phases, the two- or one dimensional navigation images may be acquired for different angles of view and/or different fields of view. In one implementation, orthogonal navigation images may be acquired for the relevant motion phases.

In one embodiment, the series of high-quality images and navigation images are acquired by the planning system, particularly by means of the imaging unit 22 contained therein, in connection with the generating of the initial treatment plan for the radiation therapy treatment of a patient. In this case, the initial treatment plan may be generated on the basis of the high-quality images of the acquired series of the high-quality images. As an alternative, the series of high-quality images and navigation images are acquired shortly before the delivery of a treatment fraction. In this case, the series may be acquired by the treatment system using the imaging unit 7 contained therein.

The acquisition of the series of high-quality images and navigation images shortly before the delivery of a treatment fraction has the advantage that changes of the anatomical configuration beyond the changes due to the motion of the target structure and/or the OARs depicted in the series can be taken into account in the adaption of the treatment plan on the basis of the series. Therefore, an acquisition shortly before a delivery of a treatment fraction is preferred over the acquisition at the time the initial planning of the treatment if such changes are expected. Examples of such changes include changes due to differences in the bladder or rectum filing at the time of a treatment fraction or at the time of the initial planning in regions of the patient body including the bladder or rectum or being located in the vicinity of the bladder or rectum.

Upon having acquired the series of high-quality and navigation images, each navigation image is associated with a corresponding high-quality image, i.e. with the high-quality image pertaining to the same phase of the motion of the target structure and/or the OARs. The association is made such that the evaluation unit 6 of the treatment system is capable of determining the associated high-quality image for each navigation image or for the plural navigation images which may be acquired for one or more motion phases. Moreover, the target structure and the relevant OARs are delineated in the high-quality images using a suitable delineation procedure. Then, the navigation images and the associated high-quality are provided to the evaluation unit 6 of the treatment system through the receiving unit 8.

In order to carry out dose accumulation during the treatment, the treatment system acquires real-time images of the region of the patient body including the target structure and the OARs during the treatment by means of the imaging unit 7 included in the treatment system. For this purpose, the control unit 5 controls the imaging unit 7 to acquire the images using the fast imaging mode. The fast imaging mode is applied in a configuration corresponding to the configuration used for acquiring the series of navigation images. This particularly means that the real-time images acquired by the imaging unit 7 have the same dimensionality as the navigation images in the series.

The images may be acquired in accordance with a division of the treatment into temporal segments such that one image is acquired during each of these sections. Preferably, the length of the segments is shorter than a treatment fraction so that each treatment fraction consists of a plurality of segments. In this way, the dose accumulation can be carried out on the basis of sub-fractional temporal segments of the treatment.

Upon acquisition of a real-time image by the imaging unit 7, the evaluation unit 6 compares the acquired images with the navigation images included in the received series of navigation images. In this comparison, the evaluation unit 6 selects the navigation image of the series of navigation images which best matches the acquired image on the basis of a predefined criterion. For this purpose any suitable matching criterion can be applied, which is known to the person skilled in the art. Using an appropriate matching criterion, the navigation image can be selected such that it essentially shows the target structure and/or the OARs in essentially the same phase of their motion as the acquired real-time image. Examples of appropriate matching criteria include criteria based on the sum of squared differences, on mutual information or cross correlation.

In case plural navigation images are acquired for one or more motion phases, the evaluation unit 6 may compare the real-time images with each of the sets of navigation images for the motion phases and determines the best matching set. This determination is likewise made on the basis of a suitable predetermined matching criterion.

Upon having selected one of the navigation images of the series pertaining to one motion phase or one set of navigation images pertaining to one motion phase, the evaluation unit 6 performs dose accumulation on the basis of the high-quality image associated with the selected navigation image or set of navigation images. This high-quality image corresponds to the high quality image associated with the same motion phase as the selected navigation image or the selected set of navigation images. Thus, the dose accumulation is not directly performed using the image acquired in accordance with the fast imaging mode but on the basis of a high-quality image identified on the basis of the acquired image. Since this high-quality image shows the target structure and the OARs in essentially the same phase of motion as the acquired real-time image, the dose accumulation can thus be made on the basis of an image having a high quality and on the basis of a good approximation of the actual current positions and contours of the target structure and the OARs.

In order to perform dose accumulation, the evaluation unit 6 may carry out DIR between the identified high-quality image and the relevant reference image in order to determine a deformation vector field transforming the high-quality image to the relevant reference image. As said above, the relevant reference image may correspond to the initial planning image, for example. The determined deformation vector field may then be used in order to perform dose accumulation.

In an alternative implementation, the DIR is not carried out upon acquisition of the real-time image. In this implementation, DIR is carried out in advance between each high-quality image and the relevant reference image in order to determine corresponding deformation vector fields. Thus, for each high-quality image of the series of high-quality images one associated deformation vector field is determined for mapping the high-quality image onto the relevant reference image. The deformation vector fields are then stored in association to the navigation images such that each vector field is associated to the navigation image that corresponds to the high-quality image on the basis of which the deformation vector field is calculated.

Upon having acquired the real-time image during the treatment in this implementation, the evaluation unit 6 determines the navigation image or the set of navigation images associated with one of the motion phases, which best matches the acquired real-time image. Then, the evaluation unit 6 selects the pre-calculated deformation vector field associated with the determined navigation image and carries out dose accumulation using the selected pre-calculated deformation vector field. This implementation has the advantage that the deformation vector field used for performing dose accumulation is more quickly available upon the acquisition of the real-time image.

In this implementation, the deformation vector fields may be pre-calculated in the evaluation unit 6 after the evaluation unit 6 has received the series of navigation images and the series of high-quality images as well as the relevant planning image. As an alternative, the deformation vector fields may be pre-computed outside the evaluation unit 6, e.g. in the planning unit 21. In this case, the evaluation unit 6 receives the series of images together with the associated deformation vector fields via the receiving unit 8.

In one embodiment, DIR is additionally performed in the evaluation unit 6 between the acquired real-time image and the selected navigation image to determine a further deformation vector field to transform the real-time image on the navigation image. This is particularly useful in case three-dimensional navigation and real-time images are acquired. However, the evaluation unit 6 may likewise calculate an estimate of the further deformation vector field on the basis of lower-dimensional navigation images. The further deformation vector field quantifies the differences between the current locations and contours of the target structure and the OARs and the locations and contours shown in the navigation image and the associated high quality image. Therefore, the further deformation vector field is used for correcting the deformation vector field determined on the basis of the high-quality images.

This may be done by determining a combined deformation vector field which consists of a combination of the further deformation vector field and the deformation vector field determined on the basis of the high-quality images. The combination is made in such a way that the resulting deformation vector field corresponds to a transformation in which the deformation vector field determined on the basis of the high-quality images is applied subsequent to the further deformation vector field. The resulting deformation vector field is then used for carrying out dose accumulation.

Upon having determined a deformation vector field in accordance with one of the embodiments described above, dose accumulation is carried out in accordance with a procedure known to a person skilled in the art. As explained above, this procedure may comprise a calculation of the radiation dose delivered to the voxels of the target structure and the OARs during the relevant temporal segment of the treatment and a calculation of the accumulated dose delivered during the treatment by mapping the voxels of the target structure and the OARs to the relevant planning image using the determined deformation vector field.

The calculation of the radiation dose delivered to the voxels of the target structure and the OARS during the relevant temporal segment of the treatment may be calculated on the basis of the high-quality image identified on the basis of the acquired real-time. If the evaluation unit 6 calculates a combined deformation vector field as explained above, the dose calculation may alternatively be performed on the basis of an image generated from the reference image using the combined deformation vector field (or its inverse). Hereby, a high-quality image can be generated which represents the actual anatomical configuration of the body region including the target structure and the OARs as shown in the acquired real-time image.

In the embodiments described above, dose accumulation can be carried out essentially in real-time. As explained above, the evaluation unit 6 may use the results of the dose accumulation procedure to determine whether the treatment goals can be fulfilled on the basis of the active treatment plan. This is case, if the sum of the accumulated dose already delivered to each voxel of the target structure and the OARs and the dose which will be delivered to the respective voxel in accordance with the active treatment plan in the remainder of the treatment corresponds to the dose goal for the voxel within predefined boundaries. If the evaluation unit 6 determines that the treatment goals can be fulfilled on the basis of the active treatment plan, it may control the treatment system to proceed with the treatment on the basis of the active treatment plan.

If the evaluation unit 6 determines that the treatment goals cannot be fulfilled on the basis of the active treatment plan, it may determine an adapted treatment plan in order to fulfill the treatment goals. The adapted treatment plan is likewise generated on the basis of the estimated accumulated radiation dose delivered to each voxel of the planning volume during the treatment. On the basis of this estimate, the adapted treatment plan is determined such that the prescribed dose is delivered to the target structure and the OARs until the end of the treatment. Moreover, the adapted treatment plan is generated on the basis of an image of the relevant region of the patient body, which at least approximately shows the current anatomical configuration of this region. In this image, the target structure and the OARs are again delineated and the adapted treatment plan is generated on the basis of these delineations. In this respect, the evaluation unit 6 may use the same image which is also used for calculating the radiation dose delivered to the target structure and the OARs as explained above.

Further, the evaluation unit 6 may use the previous treatment plan in order to generate the adapted treatment plan. For instance, in accordance with one strategy, the dose distribution corresponding to the relevant previous treatment plan is mapped from the previous planning image onto the new planning image used for the adaptation. The deformed dose distribution may then serve as a goal distribution for a re-planning procedure executed to determine the new treatment plan. In such a way a quick re-optimization of the treatment plan may be carried out. Examples of corresponding re-optimization procedure are described in the publication D. Thongphiew et al, "Comparison of online IGRT techniques for prostate IMRT treatment: adaptive vs repositioning correction", Med Phys. 36, 1651 (2009). Likewise, the plan re-optimization may be carried out in any other suitable way known to the person skilled in the art.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A treatment system for delivering an image-guided radiation therapy treatment to a moving structure included in a region of a patient body based on a treatment plan, the treatment system comprising:
    a receiving unit for receiving a series of first images of the region of the patient body in different phases of a motion of the moving structure, the series of first images being associated with a series of second images of the patient body in same phases of the motion of the moving structure as the series of first images,
    wherein the first images are acquired from a planning imaging unit in accordance with a first imaging mode and the second images are acquired from the planning imaging unit in a second imaging mode differing from the first imaging mode, wherein the first imaging mode is a 3 dimensional (3D) imaging mode and the second imaging mode is one of a 2 dimensional (2D) imaging mode or a 1 dimensional (1D) imaging mode, wherein the first images are 3D images, wherein the second images are 2D images when the second imaging mode is the 2D imaging mode, and wherein the second images are 1D images when the second imaging mode is the 1D imaging mode,
    wherein the first images and the second images are acquired using a same imaging modality as each other,
    wherein each second image is associated with a corresponding first image among the series of first images, wherein each second image and the corresponding first image pertain to a same phase of the motion of the moving structure as each other,
    a therapy imaging unit controllable to acquire a third image of the patient using the second imaging mode during the radiation therapy treatment, wherein the third image is a 2D image when the second imaging mode is the 2D imaging mode, and wherein the third image is a 1D image when the second imaging mode is the 1D imaging mode, and
    an evaluation unit configured to plan a continuation of the radiation therapy treatment upon the acquisition of the third image,
    wherein the evaluation unit is configured to compare the third image of the patient acquired using the second imaging mode during the radiation therapy treatment, with the second images which are associated with the first images, and is further configured to select a selected one of the first images based on the comparison between the third image and the second images which are associated with the first images, and is further configured to plan the continuation of the radiation therapy treatment based on data relating to the selected one of the first images.

2. The treatment system of claim 1, wherein the second imaging mode is selected such that it allows for a faster image acquisition compared with the first imaging mode.

3. The treatment system of claim 1, wherein the evaluation unit is configured to plan the continuation of the treatment on the basis of an estimated accumulated radiation dose delivered to the region in the radiation therapy treatment, the estimated accumulated dose being determined based on a deformation vector field for performing deformable image registration between the selected one of the first images and a reference image acquired in accordance with the first imaging mode.

4. The treatment system of claim 3, wherein the estimated accumulated dose is further determined based on a further deformation vector field for performing deformable image registration between the third image and a one of the second images which corresponds to the selected one of the first images.

5. The treatment system of claim 3, wherein the treatment plan is generated based on a planning image of the region of the patient body in one phase of the motion of the structure, the planning image corresponding to the reference image.

6. The treatment system of claim 3, wherein the planning of the continuation of the treatment comprises a determination of whether treatment goals for the radiation therapy treatment can be fulfilled by continuing the treatment using the treatment plan, the determination being made based on the estimated accumulated radiation dose.

7. The treatment system of claim 1, wherein either the first and second images are magnetic resonance images, or the first and second images are X-ray tomography images.

8. The treatment system of claim 1, wherein the first and second images are X-ray tomography images.

9. The treatment system of claim 1, wherein the therapy imaging unit and the planning imaging unit are two different imaging units.

10. The treatment system of claim 1, wherein the therapy imaging unit is the planning imaging unit.

11. The treatment system of claim 1, wherein the first, second, and third images are all magnetic resonance images.

12. The treatment system of claim 1, wherein the evaluation unit is configured to plan the continuation of the treatment on the basis of an estimated accumulated radiation dose delivered to the region in the radiation therapy treatment.

13. A method for operating a treatment system for delivering an image-guided radiation therapy treatment to a moving structure included in a region of a patient body based on a treatment plan, the method comprising:
receiving a series of first images of the region of the patient body in different phases of a motion of the moving structure, the series of first images being associated with a series of second images of the patient body in same phases of the motion of the moving structure as the series of first images,
wherein the first images are acquired from an imaging unit in accordance with a first imaging mode and the second images are acquired from the imaging unit in accordance with a second imaging mode differing from the first imaging mode, wherein the first imaging mode is a 3 dimensional (3D) imaging mode and the second imaging mode is one of a 2 dimensional (2D) imaging mode or a 1 dimensional (1D) imaging mode, wherein the first images are 3D images, wherein the second images are 2D images when the second imaging mode is the 2D imaging mode, and wherein the second images are 1D images when the second imaging mode is the 1D imaging mode,
wherein the first images and the second images are acquired using a same imaging modality as each other, wherein each second image is associated with a corresponding first image among the series of first images, wherein each second image and the corresponding first image pertain to a same phase of the motion of the moving structure as each other,
acquiring a third image of the patient using the second imaging mode during the radiation therapy treatment, wherein the third image is a 2D image when the second imaging mode is the 2D imaging mode, and wherein the third image is a 1D image when the second imaging mode is the 1D imaging mode,
comparing the third 2D or 1D image of the patient acquired using the second imaging mode during the radiation therapy treatment, with the second 2D or 1D images which are associated with the first 3D images,
selecting a selected one of the first 3D images based on the comparison between the third 2D or 1D image and the second 2D or 1D images which are associated with the first 3D images, and
planning a continuation of the radiation therapy treatment based on the selected one of the first 3D images.

14. A tangible nonvolatile computer readable medium having stored thereon a computer program comprising program code means for causing a computer device to carry out a method as defined in claim 13 when the computer program is executed on the computer device.

15. The method of claim 13, wherein the second imaging mode is selected such that it allows for a faster image acquisition compared with the first imaging mode.

16. The method of claim 13, comprising identifying a motion phase associated with at least one second image that best matches the third image in accordance with a predefined criterion, and selecting a first image associated to the identified motion phase as the selected one of the first images based on which the continuation of the radiation therapy treatment is planned.

17. The method of claim 13, comprising planning the continuation of the treatment on the basis of an estimated accumulated radiation dose delivered to the region in the radiation therapy treatment.

18. The method of claim 13, further comprising:
determining an estimated accumulated dose delivered to the region in the radiation therapy treatment based on a deformation vector field for performing deformable image registration between the selected one of the first images and a reference image acquired in accordance with the first imaging mode; and
planning the continuation of the treatment on the basis of the estimated accumulated radiation dose delivered to the region in the radiation therapy treatment.

19. The method of claim 13, wherein selecting a selected one of the first 3D images based on the comparison between the third 2D or 1D image, and the second 2D or 1D images which are associated with the first 3D images, comprises:
determining a second 2D or 1D image, among the second 2D or 1D images, that best matches the third 2D or 1D image in accordance with a predefined criterion;
identifying a motion phase associated with the second 2D or 1D image that best matches the third 2D or 1D image in accordance with the predefined criterion; and
identifying a first 3D image, among the first 3D images, which is associated with the identified motion phase as the selected first 3D image.

20. The method of claim 13, comprising receiving the series of first images and the series of second images prior to the radiation therapy treatment.

* * * * *